(12) United States Patent
Welborn et al.

(10) Patent No.: US 8,262,721 B2
(45) Date of Patent: Sep. 11, 2012

(54) DRAINAGE STENT AND ASSOCIATED METHOD

(75) Inventors: Kristin Welborn, Charlotte, NC (US); Thomas Nissl, Winsen/Luhe (DE)

(73) Assignee: Merit Medical Systems, Inc., South Jordan, UT (US)

( * ) Notice: Subject to any disclaimer, the term of this patent is extended or adjusted under 35 U.S.C. 154(b) by 548 days.

(21) Appl. No.: 11/433,024

(22) Filed: May 12, 2006

(65) Prior Publication Data
US 2007/0100437 A1 May 3, 2007

Related U.S. Application Data

(60) Provisional application No. 60/680,675, filed on May 13, 2005.

(51) Int. Cl.
*A61F 2/06* (2006.01)
(52) U.S. Cl. ............ 623/1.13; 623/1.11; 623/1.12; 623/1.2; 623/1.23; 623/1.35; 623/1.39
(58) Field of Classification Search .......... 623/1.15, 623/1.39, 23.64, 23.7, 1.13; 640/540, 543; 3/1.15
See application file for complete search history.

(56) References Cited

U.S. PATENT DOCUMENTS

| | | | |
|---|---|---|---|
| 5,364,340 A | 11/1994 | Coll | |
| 5,507,771 A | 4/1996 | Gianturco | |
| 5,556,414 A * | 9/1996 | Turi | 623/1.11 |
| 5,741,327 A | 4/1998 | Frantzen | |
| 5,861,027 A | 1/1999 | Trapp | |
| 6,299,635 B1 | 10/2001 | Frantzen | |
| 6,330,884 B1 | 12/2001 | Kim | |
| 6,485,508 B1 | 11/2002 | McGuinness | |
| 6,503,556 B2 | 1/2003 | Harish et al. | |
| 6,540,776 B2 | 4/2003 | Sanders Millare et al. | |
| 6,569,150 B2 | 5/2003 | Teague et al. | |
| 6,602,281 B1 | 8/2003 | Klein | |
| 6,607,554 B2 | 8/2003 | Dang et al. | |
| 6,758,860 B1 | 7/2004 | Penn et al. | |

(Continued)

FOREIGN PATENT DOCUMENTS
CA   2304578   4/1999
(Continued)

OTHER PUBLICATIONS

PCT Notification of Transmittal of the International Search Report and the Written Opinion of The International Searching Authority, or the Declaration, mailed Aug. 22, 2006 for PCT/US2006/013129 (Filed Apr. 6, 2006).

(Continued)

*Primary Examiner* — Gary Jackson
*Assistant Examiner* — Kevin Everage
(74) *Attorney, Agent, or Firm* — Stoel Rives LLP

(57) ABSTRACT

A stent for facilitating flow between a branch of a bifurcated lumen and an interior region of the stent is provided. The stent includes proximal and distal ends and an interior region defined therethrough. The stent typically includes scaffolding having a cover applied thereto. The stent also includes at least one drainage region having at least one drainage hole defined between the scaffolding and through the cover such that fluid is capable of flowing through the drainage holes. The drainage region is typically offset from the proximal and/or distal end to facilitate fluid flow between the branch of the bifurcated lumen and the interior region of the stent.

23 Claims, 5 Drawing Sheets

U.S. PATENT DOCUMENTS

| | | | |
|---|---|---|---|
| 6,786,922 | B2 | 9/2004 | Schaeffer |
| 6,852,123 | B2 | 2/2005 | Brown |
| 6,942,690 | B1 | 9/2005 | Pollock et al. |
| 2001/0025195 | A1 | 9/2001 | Shaolian et al. |
| 2002/0058988 | A1 | 5/2002 | Fischell et al. |
| 2002/0143386 | A1 | 10/2002 | Davila et al. |
| 2002/0178570 | A1 | 12/2002 | Sogard et al. |
| 2002/0198593 | A1 | 12/2002 | Gomez et al. |
| 2003/0040803 | A1 | 2/2003 | Rioux et al. |
| 2003/0072868 | A1* | 4/2003 | Harish et al. ............... 427/2.24 |
| 2003/0074049 | A1* | 4/2003 | Hoganson et al. ........... 623/1.13 |
| 2003/0074909 | A1* | 4/2003 | Heiden et al. ................ 62/195 |
| 2003/0130611 | A1 | 7/2003 | Martin |
| 2003/0176912 | A1 | 9/2003 | Chuter et al. |
| 2003/0208183 | A1 | 11/2003 | Whalen et al. |
| 2003/0212450 | A1 | 11/2003 | Schlick |
| 2003/0236567 | A1 | 12/2003 | Elliot |
| 2004/0059406 | A1* | 3/2004 | Cully et al. ................... 623/1.11 |
| 2004/0088040 | A1* | 5/2004 | Mangiardi et al. ........... 623/1.15 |
| 2004/0102837 | A1 | 5/2004 | Boyle et al. |
| 2004/0153141 | A1 | 8/2004 | Penn et al. |
| 2004/0176833 | A1* | 9/2004 | Pavcnik et al. .............. 623/1.13 |
| 2004/0215325 | A1 | 10/2004 | Penn et al. |
| 2004/0230119 | A1 | 11/2004 | Brustad et al. |
| 2004/0236404 | A1 | 11/2004 | Penn et al. |
| 2004/0256769 | A1* | 12/2004 | Walter ........................... 264/400 |
| 2005/0004657 | A1 | 1/2005 | Burgermeister |
| 2005/0154448 | A1 | 7/2005 | Cully et al. |
| 2005/0192620 | A1* | 9/2005 | Cully et al. ................... 606/200 |
| 2005/0261183 | A1* | 11/2005 | Stewart et al. ................ 514/12 |
| 2007/0276463 | A1 | 11/2007 | Nissl et al. |

FOREIGN PATENT DOCUMENTS

| | | |
|---|---|---|
| CA | 2446358 | 10/2003 |
| DE | 197 54 747 A1 | 6/1999 |
| DE | 20308672 | 9/2003 |
| DE | 20312113 | 9/2003 |
| EP | 1 472 990 A | 11/2004 |
| EP | 1550477 | 7/2005 |
| WO | WO 00/42949 | 7/2000 |
| WO | WO 01/72239 | 10/2001 |
| WO | WO 03/007781 | 1/2003 |
| WO | WO 03/057075 | 7/2003 |
| WO | WO 03/065933 | 8/2003 |
| WO | WO 03/082153 | 10/2003 |
| WO | WO2004/067764 | 8/2004 |
| WO | WO 2005/011527 | 2/2005 |

OTHER PUBLICATIONS

PCT Notification of Transmittal of the International Search Report and the Written Opinion of The International Searching Authority, or the Declaration, mailed Oct. 12, 2006 for PCT/US2006/018813 (Filed May 12, 2006).
W.L. Gore & Associates, Inc.; "Introducing The Gore Stent-Graft Family"; Jul. 2003;6 Pages.
W.L. Gore & Associates, Inc.; "Introductions for Use For: Viabil®, Biliary Endoprosthesis"; Sep. 2004; 9 pages.
W.L. Gore & Associates, Inc.; "Get In Cancer's Way, For the Treatment of Malignant Biliary Strictures";Feb. 2003; 4 pages.
W.L. Gore & Associates, Inc.; "Percutaneous Implantation Tips for Success"; Apr. 2003; 2 pages.
Office action dated Apr. 5, 2010 in U.S. Appl. No. 10/718,217.
Office action dated Aug. 26, 2010 in U.S. Appl. No. 10/718,217.
Notice of Allowance dated Sep. 16, 2010 in U.S. Appl. No. 10/674,972.
Notice of Allowance dated Dec. 9, 2010 in U.S. Appl. No. 10/718,217.
Response to Office Action dated Nov. 19, 2010 in U.S. Appl. No. 10/718,217.
European Search Report PCT/US2004/031304 dated Oct. 28, 2010.
Notice of Allowance dated Feb. 25, 2011 in U.S. Appl. No. 10/718,217.
International Search Report and Written Opinion for PCT/US2004/002719.
International Publication and Search Report for PCT/DE2004/002719.

* cited by examiner

DRAINAGE STENT AND ASSOCIATED METHOD

CROSS-REFERENCE TO RELATED APPLICATIONS

The present application claims priority U.S. Provisional Application No. 60/680,675 entitled "Drainage Stent and Associated Method," filed May 13, 2005, the contents of which are incorporated herein by reference.

BACKGROUND OF THE INVENTION

1) Field of the Invention

The present invention relates to a stent and, in particular, to a stent that is capable of facilitating fluid flow between a bifurcated lumen and the stent.

2) Description of Related Art

Stents are devices that are inserted into body lumina such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus for strictures or cancer. Vascular as well as nonvascular stenting has evolved significantly; unfortunately, there remain significant limitations with respect to the technology for stents implanted proximate to a bifurcated lumen within various portions of a patient's anatomy.

A lumen or similar conduit, which, along its course, extends a major branch vessel, is termed a "bifurcating" lumen. The structural point of bifurcation, where the main trunk lumen and its side branch lumen meet, is termed the origin of the side branch, and the structure forming the angle between the lumina is termed the "carina." Furthermore, two bifurcated side branches may converge to form a single lumina. For instance, the liver includes left and right hepatic ducts extending therefrom and that converge to form the common hepatic duct. The common hepatic duct joins with the bile duct, where the bile duct carries bile to the duodenum for digestion. The gall bladder includes a side branch (i.e., cystic duct) that extends between the gall bladder and the common hepatic duct. As such, bile may flow between the common hepatic duct and gall bladder via the cystic duct for storing bile when digestion is not occurring and between the gall bladder and bile duct when digestion occurs.

Accordingly, management of bifurcating lumina involves treatment of both the main trunk lumina across the origin of the side branch as well as the origin and/or proximal segment of the side branch. Attempts to treat bifurcated lumina have traditionally been by the serial installation of multiple stents or the simultaneous installation of modular stents (i.e., stents comprising a plurality of standardized units for use together in a cumulative group). In particular, attempts have been made to provide devices that allow the deployment of separate stents into each side branch. In addition, a bifurcated stent, such as the one disclosed in U.S. Patent Application Publication No. 20040220653 (application Ser. No. 10/427, 539), entitled "Bifurcated Medical Appliance Delivery Apparatus and Method," which is incorporated herein by reference, discloses an integrated stent that cradles the corina between the arms of the bifurcated stent as each arm of the bifurcated stent is delivered to a respective side branch.

Furthermore, complications may arise proximate to a bifurcation that require stenting, such as within the bile duct between the hepatic ducts and the duodenum. Providing a bifurcated stent, such as that described above, is typically difficult to position within each of the hepatic ducts. Moreover, if a stent is positioned within one of the hepatic ducts and along the bile duct, the unstented hepatic duct may be adversely affected, such as by limiting or eliminating the flow of bile between the unstented hepatic duct and the common hepatic duct and bile duct. In addition, similar complications may arise where a stent extends between a hepatic duct and the duodenum and across the opening of the cystic duct.

Thus, there is a need in the industry for a stent that facilitates fluid flow between a side branch of a bifurcated lumen and the stent. In addition, there is a need for a stent that is capable of being easily positioned proximate to a side branch of a bifurcated lumen requiring fluid flow between the branch and the stent.

BRIEF SUMMARY OF THE INVENTION

The invention addresses the above needs and achieves other advantages by providing a stent for a bifurcated lumen. The stent includes a drainage region that is positioned proximate to a branch of the bifurcated lumen. The drainage region includes drainage holes that facilitate fluid flow between the branch and the interior region of the stent. As such, fluid may flow in or out of the drainage holes thereby limiting complications resulting from occluding a branch lumen. A portion of the stent is also capable of being positioned adjacent to a target area within a second branch of the bifurcated lumen for supporting the target area.

In one embodiment of the present invention, a stent for facilitating flow between a branch of a bifurcated lumen and an interior region of the stent is provided. The stent includes proximal and distal ends and an interior region defined therethrough. The stent typically includes scaffolding having a cover applied thereto. The stent also includes at least one drainage region having at least one drainage hole defined between the scaffolding and through the cover such that fluid is capable of flowing through the drainage hole. The drainage region is typically offset from the proximal and/or distal end to facilitate fluid flow between the branch of the bifurcated lumen and the interior region of the stent.

In various aspects of the stent, there could be more than one drainage region positioned proximate to a respective branch lumen. For example, a drainage region could be positioned proximate to a hepatic duct and/or a cystic duct of the biliary tract. The stent scaffolding typically includes a plurality of interconnected legs and connectors, where the legs extend in rows circumferentially about the stent, and the connectors extend longitudinally between adjacent rows. A distal end of the drainage region could be offset at least one row from the distal end of the stent. In one aspect of the present invention, the distal end of the drainage region is offset at least about 2 cm from the distal end of the stent. At least a portion of the stent between the proximal end of the stent and the proximal end of the drainage region could be positioned adjacent to a target area located within a second branch of the bifurcated lumen. Radiopaque markers could be utilized to locate the stent and/or drainage region within the bifurcated lumen.

In additional aspects of the stent, the drainage region includes a plurality of drainage holes, wherein the drainage holes are defined at least partially about the circumference of the stent. Moreover, the drainage hole is typically defined through the cover and between the legs and connectors and may be various shapes such as circular or oval. The drainage hole could also be defined to substantially conform to one or more legs and connectors. Various techniques could be employed to form the drainage hole, such as a technique to penetrate the cover after applying the cover to the scaffolding, or a technique to mask areas of the stent during the application of the cover to the scaffolding.

BRIEF DESCRIPTION OF THE SEVERAL VIEWS OF THE DRAWINGS

Figure 1:
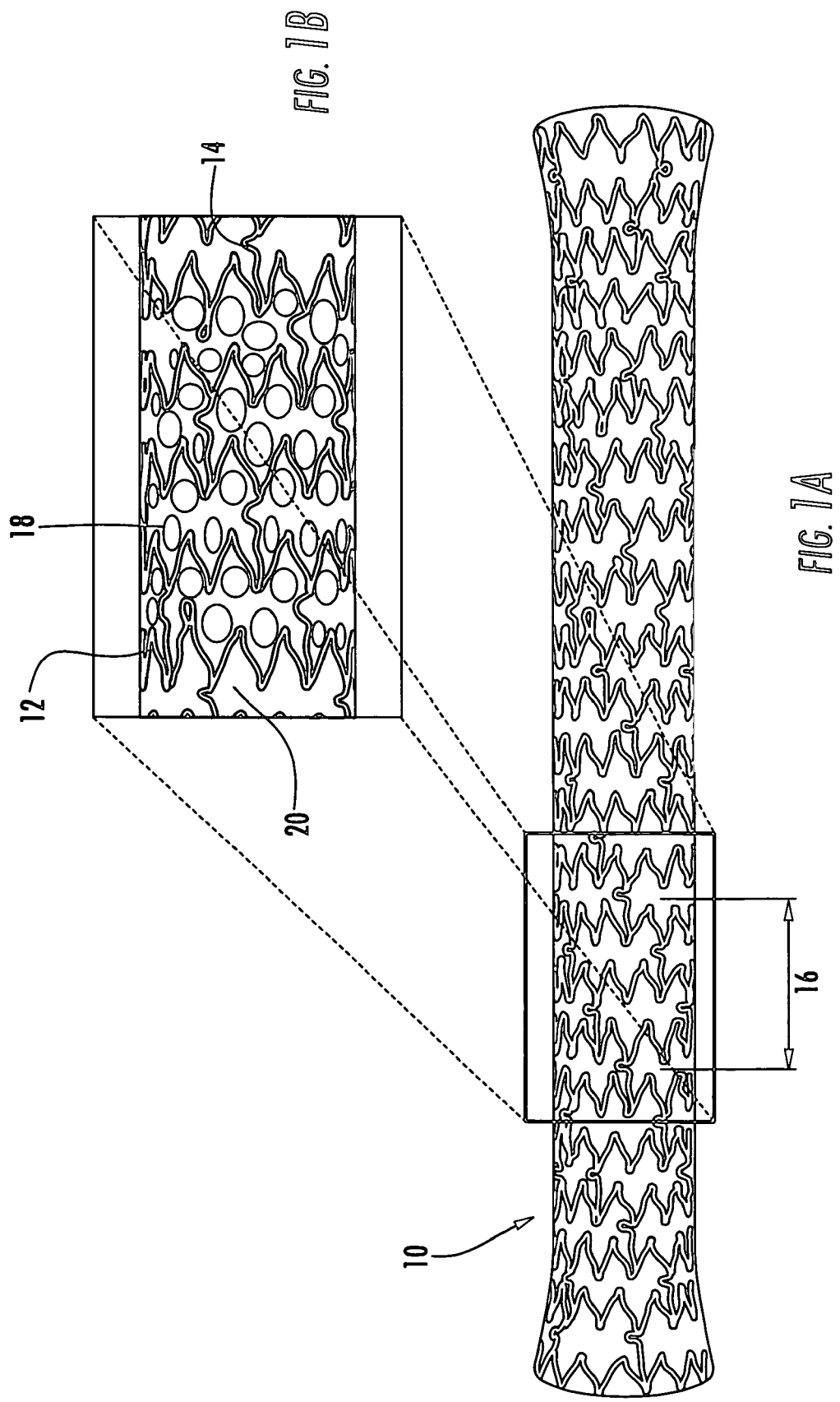
Figure 2:
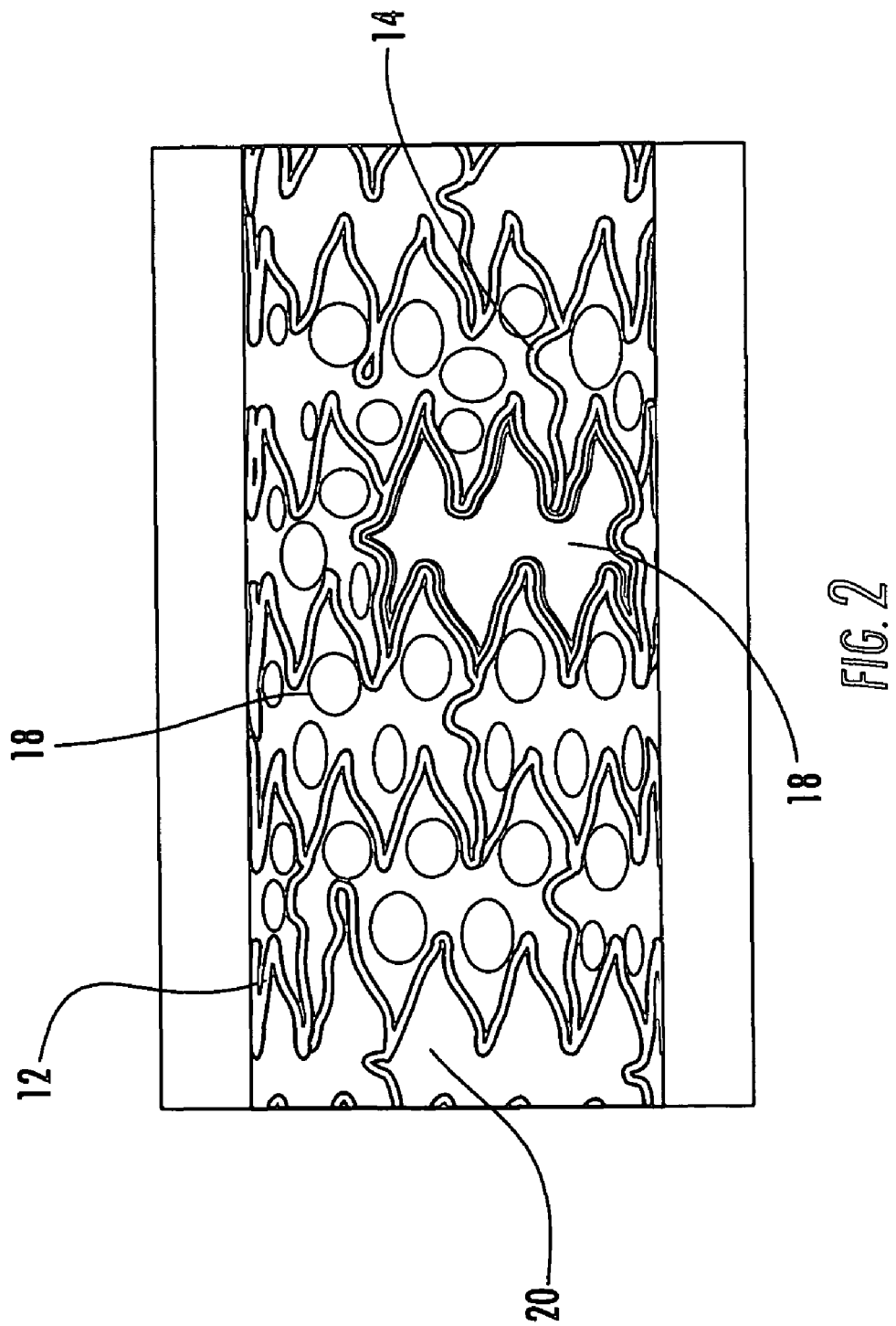
Figure 3:
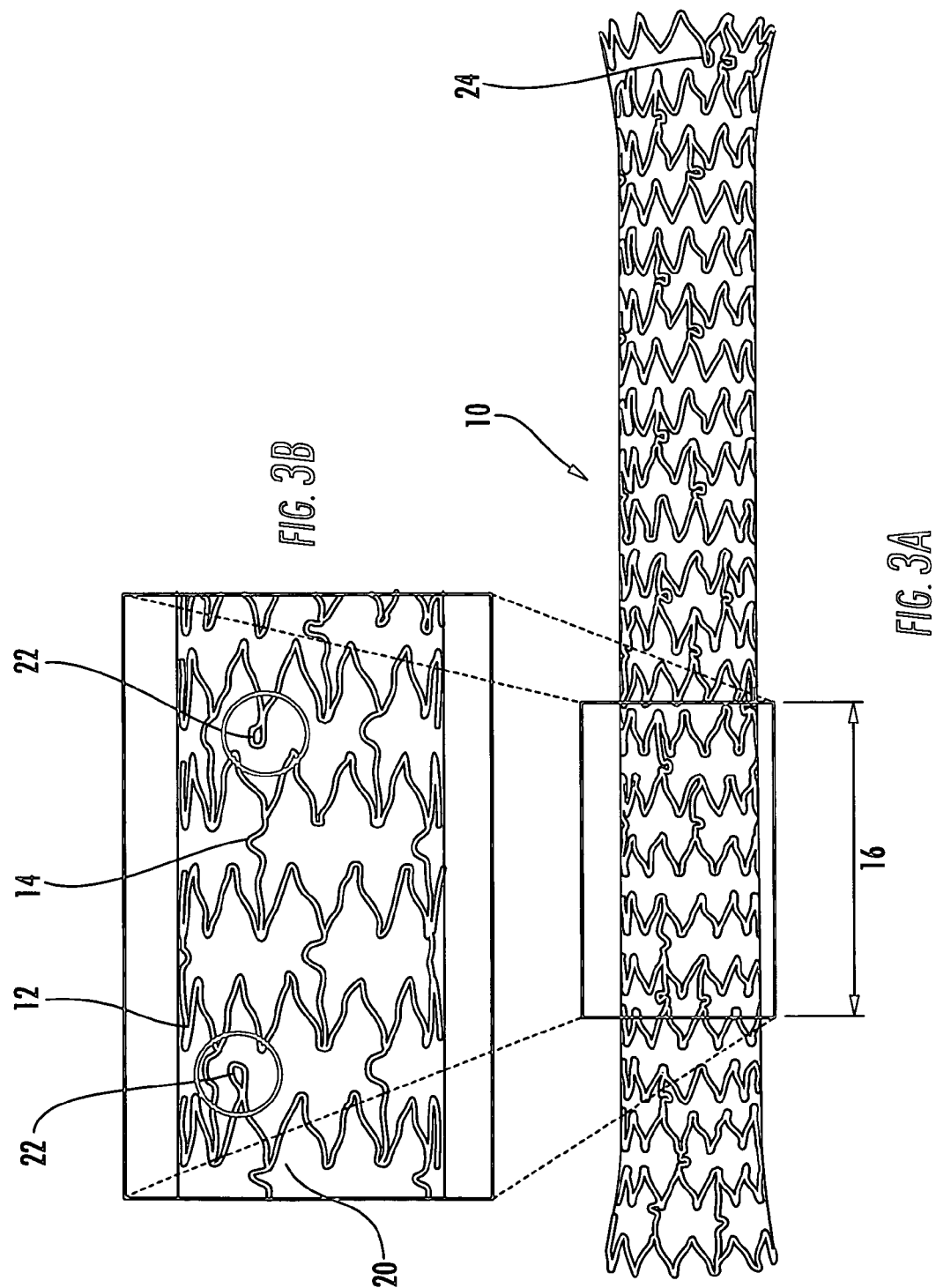
Figure 4:
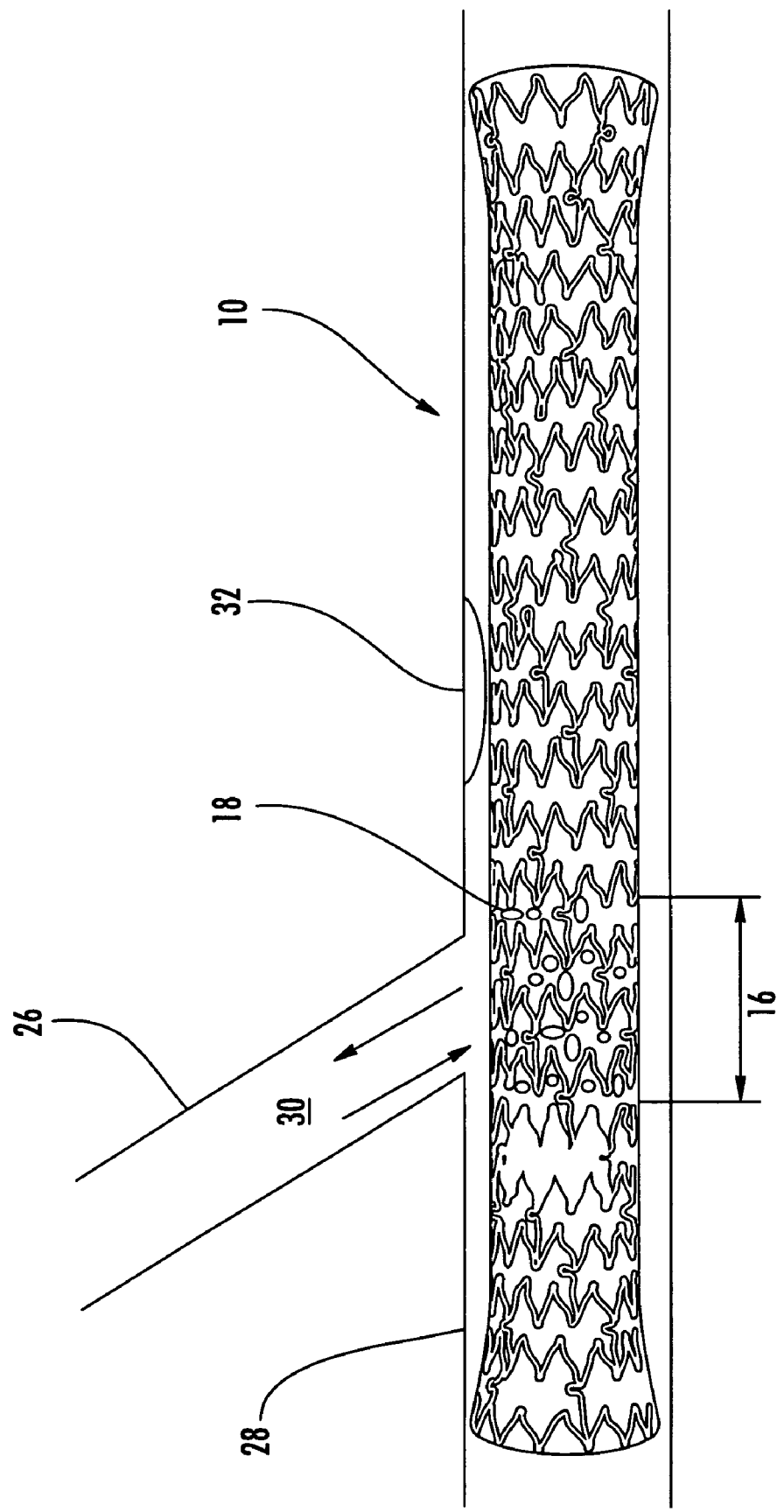
Figure 5:
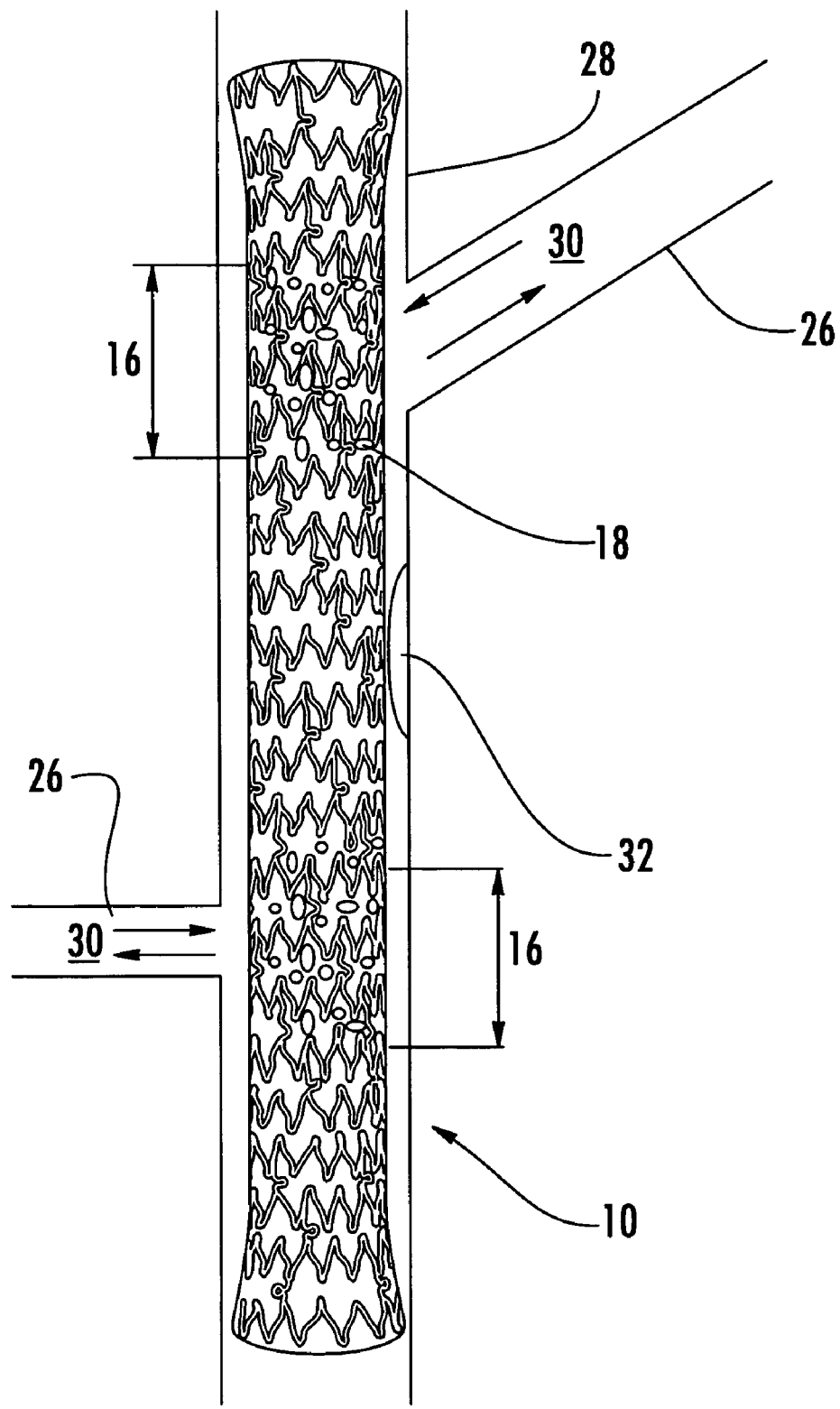

Having thus described the invention in general terms, reference will now be made to the accompanying drawings, which are not necessarily drawn to scale, and wherein:

FIG. 1A is a plan view of a stent, according to one embodiment of the present invention;

FIG. 1B is an enlarged view of a portion of the stent shown in FIG. 1A, further illustrating the drainage region;

FIG. 2 is an enlarged view of a portion of a stent illustrating a drainage region, according to another embodiment of the present invention;

FIG. 3A is a plan view of a stent, according to one embodiment of the present invention;

FIG. 3B is an enlarged view of a portion of the stent shown in FIG. 2A, further illustrating the radiopaque markers;

FIG. 4 is a plan view of a stent positioned within a bifurcated lumen, according to one embodiment of the present invention; and FIG. 5 is a plan view of a stent positioned within a bifurcated lumen, according to another embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1A-B, a stent 10 is shown having interstice geometry. The stent 10 includes a scaffolding of struts having a plurality of interconnected legs 12 and connectors 14. In particular, the stent 10 includes a series of legs 12 arranged circumferentially about the stent, as well as arranged in a series of rows along the longitudinal axis of the stent, while a plurality of connectors 14 are arranged parallel to the longitudinal axis of the stent to connect the rows together. FIG. 1A demonstrates that there is a cover 20 layer extending between the legs 12 and connectors 14, while FIG. 1B illustrates a plurality of drainage holes 18 defined along a drainage region 16 between the scaffolding and through the cover 20. The drainage holes 18 facilitate fluid flow between a side branch of the bifurcated lumen and the interior region of the stent 10.

The stent 10 is also capable of being deployed within a bifurcated lumen adjacent to a target area. "Target area," as used herein, is not meant to limiting, as the target area, could be a stricture, lesion, tumor, occlusion, or other complication where the lumen passageway has been significantly reduced. The term "stent" is also not meant to be limiting, as the stent could be any suitable implantable device capable of being deployed within a bifurcated lumen and having an interstice geometry, as described herein. It is understood that the stent 10 is applicable to a wide range of intraluminal applications. For example, the stent 10 could be implanted within bifurcated lumina of the esophagus, trachea, arteries, or the biliary tract. As used therein, the term "bifurcate," and variations thereof, are not meant to be limiting, as bifurcate corresponds to any lumen including one or more branches or ducts extending from a main trunk or duct, or a pair of branches or ducts extending from a common duct. Thus, the branches or ducts could extend at various angles from one another and be various sizes.

The legs 12 and connectors 14 of the stent 10 are preferably formed from a composite material such as Ni, C, Co, Cu, Cr, H, Fe, Nb, O, Ti and combinations thereof (e.g., Nitinol). The composite material is generally formed into a compressed tube from which the stent is etched, such as with a laser, and is formed on a suitable shaping device to give the stent the desired external geometry. The stent 10 is formed of a memory metal that facilitates flexibility of the stent 10 such that the stent may be deformed and return to its original shape.

The stent 10 is generally cylindrical, having openings at the proximal and distal ends. As illustrated in FIG. 1A, the diameter of the proximal and distal ends is slightly larger than the diameter of longitudinal portion of the stent extending therebetween. The larger diameter portions at each of the proximal and distal ends of the stent 10 provides increased fixation of the stent following deployment within the lumen. Barbs, anchors, or the like extending from the exterior surface of the stent could also be employed if desired to help fixate the stent 10 within the lumen. In the event the stent 10 is to be shaped to the dimensions of a particular lumen, optical photography, and/or optical videography of the target lumen may be conducted prior to stent formation. The interstice geometry of the stent 10 then can be formed in accordance with the requirements of that target lumen.

It should be pointed out that, unlike the use of differing shape memory materials to change regions of a stent 10, stents in accordance with the present invention can take on an infinite number of characteristic combinations of interstice geometry by changing angles, segment lengths, and segment thicknesses during the etching and forming stages of stent engineering or during post formation processing and polishing steps. Moreover, by modifying the geometry of the legs 12 and connectors 14, additional functionality may be achieved. For instance, FIGS. 1B and 2B demonstrate that a connector 14 extends between adjacent rows of legs 12. However, each connector 14 does not extend further to an additional row of legs 12. Rather, each connector 14 is spaced approximately four legs 12 from one another along the same two rows of legs, as well as between adjacent rows of legs. This configuration of connectors 14 provides flexibility, while also reducing the incidence of foreshortening of the stent during and after deployment.

The cover 20 is typically a polymer, such as polyurethane (e.g., polycarbonate urethane, or Chronoflex® manufactured by Cardiotech International), silicone, or silicone with a polytetrafluoroethylene ("PTFE") coating, that is applied over the legs 12 and connectors 14 to provide a predetermined shape for the stent 10, as well as graft each of the legs and connectors into a unitary structure. The cover 20 typically does not inhibit flexing or radial expansion of the stent 10. However, it is possible to make the cover 20 affect the flexing and radial expansion of the stent 10. The cover 20 typically forms a thin film when applied to the stent 10.

The cover 20 is applied to the scaffolding using a dipping process. The cover 20 forms a thin layer over the scaffolding such that a portion of the scaffolding is raised above the surface of the cover within the openings between the legs 12 and connectors 14. However, the interior of the stent remains substantially smooth. Providing a raised scaffolding promotes cilia action by allowing cilia movement between stent 10 struts, while a smooth interior surface promotes fluid flow through the interior region of the stent and prevents tissue ingrowth into the stent.

FIG. 1A illustrates that after applying the cover 20 to the stent 10 scaffolding, a portion of the cover may be folded back over on itself at the proximal and/or distal ends of the stent. The cover 20 in FIG. 1A is shown as folding back over a first row of legs 12 circumferentially about the stent 10, although the cover could fold back various distances, such as along the ends 10 of the legs proximate to the proximal and/or distal ends of the stent, along several rows of legs and/or connectors 14, or not at all. Folding the cover 20 ensures that the proximal and distal ends of the stent 10 are smooth. In addition, folding the cover 20 prevents the ends of the legs 12 from interlocking with one another during manufacturing or manipulation of the stent 10. However, the cover 20 may be applied to the stent 10 scaffolding so that the cover does not necessarily fold back on itself.

Any number of configurations of stents 10 could be incorporated and still be within the present scope of the invention. An exemplary embodiment of the interstice geometry of a stent 10 and methods of manufacturing the stent is disclosed in U.S. Patent Publication No. 20040127973 (application Ser. No. 10/674,972), entitled "Removable Biliary Stent," which is assigned to the present assignee and is incorporated herein by reference. Thus, the interstice geometry of the stent 10 should not be limited to that depicted in the disclosed Figures, as any number of configurations of interstice geometry could be employed with the present invention to achieve various degrees of rigidity and functionality. U.S. Patent Publication No. 20040122511 (application Ser. No. 10/669,450) entitled "Coated Stent with Geometry Determined Functionality and Method of Making the Same," which is assigned to the present assignee, is also incorporated herein by reference, describes a cover 20 that may be employed with the present invention, including the types of materials and properties suitable for the cover, as well as the process of manufacturing the stent 10.

FIG. 1B demonstrates that the stent 10 includes drainage holes 18 defined in the cover 20 along a drainage region 16. The drainage holes 18 are defined between the legs 12 and connectors 14 and completely through the cover 20. The drainage holes 18 are typically defined within the cover 20 circumferentially about the stent 18 and longitudinally along the drainage region 16 such that the drainage holes are located about the entire circumference of the stent. Providing drainage holes 18 about the entire circumference of the stent 10 allows a user to deploy the stent within a bifurcated lumen without having to position the drainage holes in a particular orientation.

FIG. 1B also illustrates that the drainage holes 18 are circular or oval, while FIG. 2 shows a drainage hole that substantially follows a contour between a segment defined by adjacent legs 12 and connectors 14. In addition, the drainage holes 18 may be defined in a predetermined pattern or arbitrarily along the drainage region 16. Thus, the drainage holes 18 may be sized and configured to achieve a particular flow rate of fluid between a branch of a bifurcated lumen and the interior of the stent 10, as well as limit the amount of fluid buildup within the drainage holes. For instance, with respect to the biliary tract, if the drainage holes 18 are too small, the flow of bile may become stagnant, which can cause bacteria formation and viscous bile buildup, thus further blocking the flow of bile. As such, the drainage region 16 and drainage holes 18 are particularly configured to promote fluid flow while decreasing the incidence of clogging or tissue ingrowth proximate to the drainage holes.

The drainage holes 18 may be various sizes and configurations, such as circular, oval, rectangular, or triangular. In addition, the drainage region 16 may be various lengths along the stent 10 and offset from the distal or proximal end of the stent at various distances. Furthermore, there may be more than one drainage region 16 defined in the stent 10, such as when the stent is positioned proximate to more than one bifurcated lumen, as shown in FIG. 5. Thus, a drainage region 16 could be offset from each of the proximal and distal ends of the stent 10, while the region located between the drainage regions is positioned proximate to a target area 32. For instance, a first drainage region 16 offset from a distal end of the stent could be positioned proximate to a hepatic duct, while a second drainage region could be positioned proximate to the opening of the cystic duct of the gallbladder.

Although the drainage holes 18 are shown as being formed about the entire circumference of the stent 10 along the drainage region 16, the drainage holes could be formed partially about the circumference of the stent. For example, the drainage holes 18 could be formed proximate to the opening of a branch of a bifurcated lumen to allow fluid to flow between the branch and the interior of the stent. Radiopaque markers or other deployment techniques could be employed to ensure that the drainage holes 18 are properly aligned with the opening of the branch of the bifurcated lumen.

The drainage holes 18 could be formed using various techniques. For example, the drainage holes 18 could be formed subsequent to applying the cover 20 to the scaffolding using a pin, punch, laser, or similar technique to penetrate the thickness of the cover. Moreover, the drainage holes 18 could be formed while applying the cover 20 to the scaffolding, such as by masking or otherwise covering areas corresponding to the drainage holes during the dipping process so that the coating is unable to form in the masked or covered areas.

FIGS. 3A and 3B illustrate that radiopaque markers 22 may be utilized to locate the drainage region 16 proximate to a branch of a bifurcated lumen. The radiopaque markers 22 are typically eyelets defined at an intersection of adjacent legs 12. Furthermore, FIG. 3A shows that radiopaque markers 24 may be located towards the proximal end of the stent 10 to aid in positioning the stent within the bifurcated lumen. The radiopaque markers 24 are generally defined on a first row of legs 12 at the proximal end of the stent 10 where a pair of legs intersects. However, the radiopaque markers 24 are typically positioned between rows of adjacent legs 12 such that the radiopaque markers are not located at the most proximal end of the stent 10 (i.e., at the proximal opening of the stent). The radiopaque markers 22 and 24 could be defined integral with adjacent legs 12 and/or connectors 14 or attached to the scaffolding in a subsequent processing step, such as by attaching one or more tantalum markers to the scaffolding via welding.

It is understood that the radiopaque markers 22 and 24 should not be limited to that shown in FIGS. 3A and 3B, as the markers could be various sizes and configurations for positioning the stent 10 and drainage region 16 within a bifurcated lumen. Thus, there could be one or more radiopaque markers 22 and 24, the markers could be various shapes such as circular or rectangular, and the markers could be various sizes depending on the type of stent and location of the bifurcated lumen. Moreover, the radiopaque markers 24 could be defined at the proximal and/or distal end of the stent 10, while the markers 22 could be defined at the proximal and/or distal end of the drainage region 16.

FIG. 4 depicts a stent 10 positioned within a bifurcated lumen. More particularly, the drainage region 16 is positioned proximate to a branch 26 extending from a main trunk 28 lumen. As shown by the arrow 30, fluid flowing from the branch 26 is capable of flowing through the drainage holes 18 and into the interior region of the stent 10. Similarly, fluid is also capable of flowing from the interior region of the stent 10, through the drainage holes 18, and into the branch 28. Thus, the stent 10 is only positioned within the trunk 28 of the bifurcated lumen, rather than both the trunk and the branch, which allows for easier placement. The stent 10 is also positioned proximate to a target area 32 where the lumen passageway of the trunk has been reduced. Typically, at least a portion of the region of the stent 10 between the proximal end of the stent and the proximal end of the drainage region 16 would be positioned proximate to a target area 32.

Furthermore, FIG. 4 demonstrates that a portion of the distal end of the stent 10 extends beyond the drainage region 16. For instance, there could be about a 2 cm gap between the distal end of the stent 10 and the distal end of the drainage region 16. Typically, the distal end of the drainage region 16 is offset at least five rows of legs 12 from the distal end of the stent 10, although the drainage region could be offset various distances, such as at least one row of legs from the distal end of the stent. Providing a gap at the distal end of the stent 10 provides easier placement of the drainage region 16 proximate to the branch 26 and increased fixation of the stent within the trunk 28 lumen. However, if necessitated by a particular bifurcated lumen, the drainage holes 18 could be defined proximate to the distal and/or proximal ends of the stent 10.

It is understood that the stent 10 could also be positioned within a branch 26 rather than the trunk 28 of a bifurcated lumen or any other location where a lumen is bifurcated. For example, a distal end of the stent 10 could be positioned partially within a first hepatic duct, while the proximal end of the stent could be positioned proximate to the duodenum. The drainage region 16 would be positioned proximate to the opening of the second hepatic duct to facilitate flow of bile from the second hepatic duct and into the interior of the stent 10. Moreover, the drainage region 16 could be positioned within the biliary duct and proximate to the opening of the cystic duct to allow two-way flow of bile into and out of the openings 18.

The stent 10 is deployed within a bifurcated lumen using techniques known to those skilled in the art. For example, the stent 10 is typically contracted to a smaller first diameter from a relaxed position. Once contracted, the stent 10 is positioned within a delivery device, such as a catheter or tube that may be inserted within the bifurcated lumen. For example, a delivery device could be used to position and deploy the stent 10 within the bifurcated lumen. An example of a delivery device suitable for implanting the duodenum stent is disclosed in U.S. Patent Application Publication No. 20040193243, entitled "Medical Appliance Optical Delivery and Deployment Apparatus and Method," which is assigned to the present assignee and incorporated herein by reference. Similarly, techniques and devices known to those skilled in the art used to locate, contract, and/or remove the stent 10 from the bifurcated lumen may be employed with the present invention. For example, various imaging techniques, such as cholangiography, could be utilized to determine whether a branch 26 may be occluded by placing the stent within the trunk 28.

The stent 10 is typically introduced orally with a delivery device, through a lumen, and proximate to a target area within a bifurcated lumen. The smaller diameter portion of the stent 10 is positioned proximate to the target area such that when the stent is deployed from the catheter or tube, the stent, if formed from an expansible material, can expand to receive the target area and even expand the diameter of the target area.

Similarly, the larger diameter portions of the stent 10 are positioned proximally and distally of the target area and when deployed from the delivery device, will expand to contact the healthy tissue of the lumen. Additionally, the drainage region 16 is positioned proximate to an opening of a branch of the bifurcated lumen such that fluid flowing through the branch may flow through the drainage holes 18 and into the interior region of the stent 10 or vice versa.

Embodiments of the present invention provide several advantages. For example, because the stent 10 is not required to be bifurcated to conform to a bifurcated lumen, the stent is easier to manufacture and position within the lumen. As such, the stent 10 is not dependent on the configuration of a particular bifurcated lumen, as the stent is only required to extend through one branch of a bifurcated lumen. Similarly, multiple stents are not required to stent each branch of a bifurcated lumen. In addition, the stent 10 is adaptable to any number of bifurcated lumina and is capable of being customized to achieve a particular flow rate. As such, the drainage holes 18 are configured to substantially mimic the natural flow of fluid within the bifurcated lumen while also providing stability and flexibility for stenting a target area within the lumen.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An implantable device for facilitating fluid flow between a branch of a bifurcated lumen and an interior region of the implantable device, the implantable device comprising:

a scaffolding of struts formed from a tube of memory material and having a proximal end and a distal end, wherein the scaffolding comprises a plurality of interconnected legs and connectors, and wherein the legs extend in circumferential rows about the implantable device, and the connectors extend longitudinally between adjacent rows;

a cover applied to and between the scaffolding of struts to define an interior region within the scaffolding; and at least one drainage region having a proximal end, a distal end, wherein the drainage region is offset from the proximal and distal ends of the scaffolding to facilitate fluid flow between the branch of the bifurcated lumen and the interior region of the scaffolding, and wherein the drainage region comprises:

at least one drainage hole defined between the scaffolding and through the cover such that fluid is capable of flowing through the drainage hole, wherein the at least one drainage hole has a periphery that follows a contour defined by a first plurality of interconnected legs of adjacent rows of the scaffolding and a first pair of connectors extending therebetween, such that all the legs and connectors are located outside of the periphery of the at least one drainage hole; and a plurality of supplemental drainage holes defined between the scaffolding and through a portion of the cover bounded by a second plurality of interconnected legs of adjacent rows of the scaffolding and a second pair of connectors extending therebetween, wherein each of the supplemental drainage holes has a periphery spaced from the second plurality of interconnected legs of adjacent rows and the second pair of connectors extending therebetween, such that fluid is capable of flowing through each of the plurality of supplemental drainage holes.

2. The implantable device according to claim 1, wherein the distal end of the drainage region is offset a plurality of rows of legs from the distal end of the scaffolding to define a gap therebetween such that no drainage holes are defined in the gap.

3. The implantable device according to claim 1, wherein the distal end of the at least one drainage region is offset at least about 2 cm from the distal end of the scaffolding.

4. The implantable device according to claim 1, further comprising a plurality of drainage regions spaced apart from one another about the entire circumference of the scaffolding, wherein each drainage region is configured to be positioned proximate to a respective branch of a bifurcated lumen.

5. The implantable device according to claim 4, wherein the plurality of drainage regions are configured to be positioned proximate to at least one of a hepatic duct and a cystic duct of the biliary tract.

6. The implantable device according to claim 1, wherein at least a portion of the implantable device between the proximal end of the scaffolding and the proximal end of the at least one drainage region is configured to be positioned adjacent to a target area located within a second branch of the bifurcated lumen.

7. The implantable device according to claim 1, wherein the scaffolding comprises at least one radiopaque marker integrally formed in the scaffolding proximate to at least one of the proximal and distal ends of the drainage region.

8. The implantable device according to claim 7, wherein each radiopaque marker comprises an eyelet integrally formed in the scaffolding and offset proximally from the distal end and offset distally at the proximal end thereof.

9. The implantable device according to claim 1, wherein the cover comprises a polymeric material.

10. A method for manufacturing an implantable device for facilitating fluid flow between a branch of a bifurcated lumen and an interior region of the implantable device, the method comprising:
    forming a scaffolding from a tube of memory material having a proximal end and a distal end, wherein the scaffolding comprises a plurality of interconnected legs and connectors, a plurality of the connectors comprising a pair of curved inclined sections; and
    wherein the legs extend in circumferential rows about the implantable device, and the connectors extend longitudinally between adjacent rows;
    applying a cover to and between the scaffolding of struts to define an interior region within the scaffolding; and
    defining at least one drainage region offset from the proximal and distal ends of the scaffolding to facilitate fluid flow between the branch of the bifurcated lumen and the interior region of the implantable device, and wherein the drainage region comprises:
        at least one drainage hole defined between the scaffolding and through the cover such that fluid is capable of flowing through the drainage hole, wherein the at least one drainage hole has a periphery that follows a contour defined by a first plurality of interconnected legs of adjacent rows of the scaffolding and a first pair of connectors extending therebetween, such that all the legs and connectors are located outside of the periphery of the at least one drainage hole; and
        a plurality of supplemental drainage holes defined between the scaffolding and through a portion of the cover bounded by a second plurality of legs of adjacent rows of the scaffolding and a second pair of connectors extending therebetween, wherein each of the supplemental drainage holes has a periphery spaced from the second plurality of legs of adjacent rows and the second pair of connectors extending therebetween, such that fluid is capable of flowing through each of the plurality of supplemental drainage holes.

11. The method according to claim 10, wherein forming comprises etching a plurality of interconnected legs and connectors.

12. The method according to claim 11, wherein defining comprises defining a distal end of the drainage region offset a plurality of rows of legs from the distal end of the scaffolding to define a gap therebetween such that no drainage holes are defined in the gap.

13. The method according to claim 11, wherein defining comprises defining the at least one drainage hole through the cover and between the legs and connectors.

14. The method according to claim 10, wherein defining comprises defining a plurality of drainage regions spaced apart from one another about the entire circumference of the scaffolding.

15. The method according to claim 10, wherein forming comprises integrally forming at least one radiopaque marker in the scaffolding proximate to at least one of a proximal end and a distal end of the drainage region.

16. The method according to claim 15, wherein forming comprises integrally forming each radiopaque marker in the scaffolding at a location offset proximally from the distal end and offset distally at the proximal end thereof.

17. The method according to claim 10, wherein applying comprises dipping the scaffolding within a polymeric material.

18. The method according to claim 10, wherein defining comprises penetrating the cover after applying the cover to the scaffolding to define the at least one drainage hole.

19. The method according to claim 10, wherein defining comprises masking at least a portion of the scaffolding during the applying step to define the at least one drainage hole.

20. An implantable device for facilitating fluid flow between a branch of a bifurcated lumen and an interior region of the implantable device, the implantable device comprising:
    a scaffolding of struts formed from a tube of memory material and having a proximal end and a distal end, wherein the scaffolding comprises a plurality of interconnected legs and connectors, and wherein the legs extend in rows circumferentially about the implantable device, and the connectors extend longitudinally between adjacent rows, a plurality of the connectors curving continuously along their length;
    a cover applied to and between the scaffolding of struts to define an interior region within the scaffolding;
    at least one drainage hole defined between the scaffolding and through the cover such that fluid is capable of flowing through the drainage hole, wherein the at least one drainage hole has a periphery that follows a contour defined by a first plurality of interconnected legs of adjacent rows of the scaffolding and a first pair of connectors extending therebetween, such that all the legs and connectors are located outside of the periphery of the at least one drainage hole; and
    a plurality of supplemental drainage holes defined between the scaffolding and through a portion of the cover bounded by a second plurality of interconnected legs of adjacent rows of the scaffolding and a second pair of connecters extending therebetween, wherein each of the supplemental drainage holes has a periphery spaced from the second plurality of legs of adjacent rows and the second pair of connecters extending therebetween, such that fluid is capable of flowing through each of the supplemental drainage holes and such that all the legs and connectors are located outside of a periphery of each of the supplemental drainage holes, wherein each of the supplemental drainage holes is configured to facilitate fluid flow between the branch of the bifurcated lumen and the interior region of the scaffolding, wherein the plurality of supplemental drainage holes are spaced apart from one another about the entire circumference of the scaffolding and are offset a plurality of rows of legs from the distal end of the scaffolding to define a gap therebetween such that no drainage holes are defined in the gap.

21. The implantable device according to claim 20, wherein the plurality of drainage holes are defined through the cover and between the legs and connectors.

22. The implantable device according to claim 20, wherein at least one of the plurality of supplemental holes is circular or oval in shape.

23. The implantable device according to claim 20, wherein the scaffolding comprises at least one radiopaque marker, and wherein each radiopaque marker is integrally formed in the scaffolding and offset from the distal and proximal ends thereof.

* * * * *